United States Patent
Dhan

(10) Patent No.: US 9,482,683 B2
(45) Date of Patent: Nov. 1, 2016

(54) SYSTEM AND METHOD FOR SEQUENTIAL TESTING ACROSS MULTIPLE DEVICES

(71) Applicant: Wipro Limited, Bangalore (IN)

(72) Inventor: Pratap Chandra Dhan, Odisha (IN)

(73) Assignee: Wipro Limited, Bangalore (IN)

( * ) Notice: Subject to any disclaimer, the term of this patent is extended or adjusted under 35 U.S.C. 154(b) by 297 days.

(21) Appl. No.: 14/300,852

(22) Filed: Jun. 10, 2014

(65) Prior Publication Data

US 2015/0301071 A1    Oct. 22, 2015

(30) Foreign Application Priority Data

Apr. 22, 2014 (IN) .......................... 2043/CHE/2014

(51) Int. Cl.
| | |
|---|---|
| G01R 31/28 | (2006.01) |
| G01R 31/00 | (2006.01) |
| G01N 35/00 | (2006.01) |
| G06F 11/36 | (2006.01) |
| G01R 31/317 | (2006.01) |
| G06F 11/34 | (2006.01) |

(52) U.S. Cl.
CPC ....... *G01N 35/0092* (2013.01); *G01R 31/2834* (2013.01); *G06F 11/3688* (2013.01); *G01R 31/31705* (2013.01); *G01R 31/31707* (2013.01); *G06F 11/3466* (2013.01)

(58) Field of Classification Search
CPC .......... G06F 11/3688; G06F 11/3466; G06F 11/36; G06F 11/3612; G06F 11/3664; G06F 11/3692; G01N 35/0092; G01R 31/2834; G01R 31/31705; G01R 31/31707; G01R 31/3183; G01R 31/318307; G01R 31/318392; G01R 31/318522

USPC ...... 324/551, 537, 500, 3.1, 76.11; 702/108, 702/117, 118, 121, 123; 717/115, 124, 127, 717/131

See application file for complete search history.

(56) References Cited

U.S. PATENT DOCUMENTS

| | | | |
|---|---|---|---|
| 6,014,760 A | 1/2000 | Silva et al. | |
| 7,287,190 B2 | 10/2007 | Rosenman et al. | |
| 7,299,451 B2 | 11/2007 | Dygon et al. | |
| 7,353,439 B2 | 4/2008 | Lin | |
| 8,166,458 B2 | 4/2012 | Li et al. | |
| 8,204,498 B1 * | 6/2012 | Smith ................. | G06F 11/2294 455/423 |
| 8,560,273 B2 | 10/2013 | Brown et al. | |
| 8,566,648 B2 | 10/2013 | Schroeder | |
| 2003/0131285 A1 | 7/2003 | Beardsley et al. | |
| 2006/0080638 A1 | 4/2006 | Fiore | |
| 2007/0022324 A1 | 1/2007 | Chang et al. | |
| 2012/0185823 A1 * | 7/2012 | Monza ................ | G06F 9/45516 717/115 |
| 2014/0282433 A1 * | 9/2014 | Eilam ................. | G06F 11/3688 717/131 |
| 2014/0282434 A1 * | 9/2014 | Eilam ................. | G06F 11/3688 717/131 |

* cited by examiner

*Primary Examiner* — Hoai-An D Nguyen
(74) *Attorney, Agent, or Firm* — LeClairRyan, a Professional Corporation

(57) ABSTRACT

Disclosed herein are systems and methods for sequential testing across multiple devices. In one implementation, the method includes analyzing test device requirements, received from a plurality of user devices, to generate automation scripts for test automation. Further, the method includes allocating testing devices, from among the plurality of user devices, for the sequential testing based on availability of the plurality of user devices and the test device requirements. Further, the method includes determining a sequential schedule based on at least one of a waiting time for the testing devices, a priority assigned to the testing devices and the automation scripts, intermediate data, an execution status, and a device status.

18 Claims, 7 Drawing Sheets

SYSTEM AND METHOD FOR SEQUENTIAL TESTING ACROSS MULTIPLE DEVICES

CROSS-REFERENCE TO RELATED APPLICATIONS

This application claims the benefit of Indian Patent Application Filing Number 2043/CHE/2014, filed on Apr. 22, 2014, which is hereby incorporated by reference in its entirety.

FIELD

The present subject matter is related, in general to automation testing devices and, in particular, but not exclusively to methods and systems for sequential testing across multiple devices.

BACKGROUND

Automated testing is generally performed to identify if there is any bugs in source codes and to check whether a software application installed on a device is functioning properly or not. In automated testing, test scripts are written to check whether results of the automated testing are in accordance to expected outputs. Further, any bugs in the source code or software application, identified during automated testing, are reported to concerned stakeholders, such as a test engineer, so that they can be eliminated from the source code. The test scripts can be run recursively to test the functioning of software. The automated testing may comprise various tasks, such as checking the syntax of the source codes, checking outputs of the software application, and checking behavior of the software application for predefined inputs.

Nowadays, organizations are using wide ranges of devices having various platforms to meet their requirements. In such cases, automated testing is typically carried out for each of the devices independently to check whether the device and/or an application installed on the device is working properly.

SUMMARY

Disclosed herein are systems and methods for sequential testing across multiple devices. In one example, the system, for sequential testing across multiple devices, comprises a processor, a memory communicatively coupled to the processor, wherein the memory stores processor-executable instructions, which, on execution, cause the processor to analyze test device requirements, received from a plurality of user devices, to generate automation scripts for test automation. The processor-executable instructions, on execution, further cause the processor to allocate testing devices, from among the plurality of user devices, for the sequential testing based on availability of the plurality of user devices and the test device requirements. The processor-executable instructions, on execution, further cause the processor to determining a sequential schedule based on at least one of a waiting time for the testing devices, a priority assigned to the testing devices and the automation scripts, intermediate data, an execution status, and a device status.

In an aspect of the invention, the method for sequential testing across multiple devices comprises analyzing test device requirements, received from a plurality of user devices, to generate automation scripts for test automation. Further, the method comprises allocating testing devices, from among the plurality of user devices, for the sequential testing based on availability of the plurality of user devices and the test device requirements. Further, the method comprises determining a sequential schedule based on at least one of a waiting time for the testing devices, a priority assigned to the testing devices and the automation scripts, intermediate data, an execution status, and a device status.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1A:
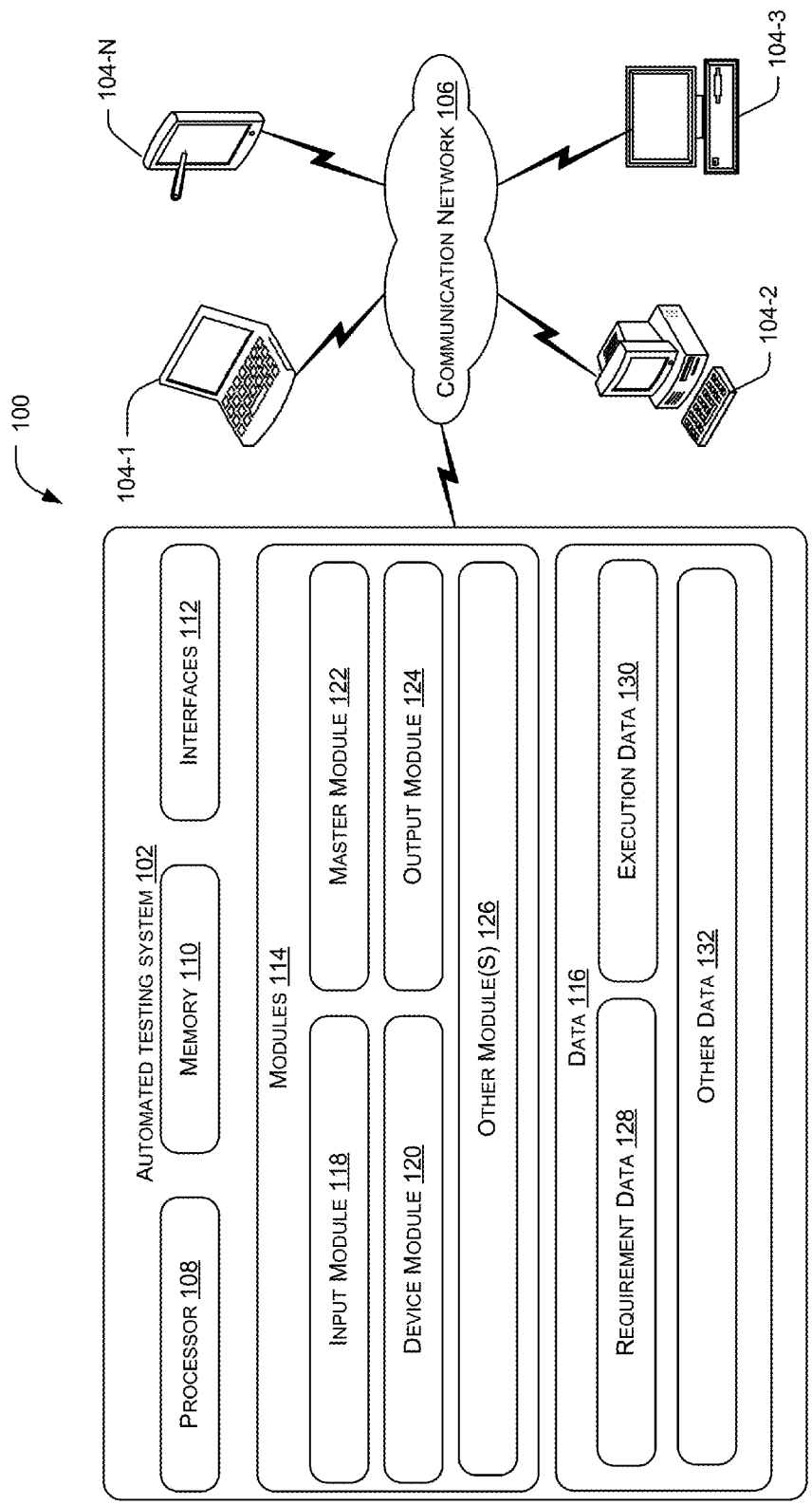
FIG. 1(a) illustrates a network environment implementing an automated sequential testing system for sequential testing across multiple devices, according to an embodiment of the present subject matter.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

Systems and methods for sequential testing across multiple devices are described herein. The systems and methods may be implemented in a variety of computing systems. The computing systems that can implement the described method(s) include, but are not limited to a server, a desktop personal computer, a notebook or a portable computer, a mainframe computer, and in a mobile computing environment. Although the description herein is with reference to certain computing systems, the systems and methods may be implemented in other computing systems, albeit with a few variations, as will be understood by a person skilled in the art.

Generally in an organization's network, different types of computing devices, such as mobile phones, laptops, desktop computers, and tablets, are present. These computing devices may have different platforms installed on them along with various software applications, which allow a user to perform certain tasks. In one scenario, a software application may be installed on the computing devices, such as a laptop, a mobile phone, a desktop application or any portable device. To test consistency of the software application across different computing devices, automation tools performs the testing for each of the computing device individually. In another scenario, a cloud storage application can be accessed using different computing device. In such cases, a user may sync a file in cloud and then may want to check file availability in all the devices. So, generally when test automation has to be done to check the file availability, the user has to automate separately in the each of the devices.

Typically, conventional automation testing tools work in an isolated manner. For example, a web automation tool does not interact with an iPhone automation tool and an iPhone automation tool doesn't interact with a PC automation tool. Further, during automation testing across the devices, it is possible that a software application may need data from other applications to function. This requirement of the data from other software applications creates a dependency between the two applications. So, if test automation has to be done on the software applications which are dependent on other software applications, then the user need to get the data manually from the other software applications before starting the automation testing of the software application. The conventional automation test tools generally do not co-ordinate the execution of a task across multiple devices which have dependency on each other.

In an example, say a user purchased a product online using a web browser on desktop computer. The user now wants to check its status in a native app of the online store on his smart phone. If test automation has to be done on above example, a test engineer may first need to automate the web browser and then the smart phone separately with manual exchange of data, for example an order ID, between these two devices. Hence, the conventional automation testing tools lead to tedious as well as sub-optimal test automation system development.

The present subject matter discloses systems and methods for sequential testing across multiple devices. The present subject matter performs the sequential test automation along with automatic exchange of intermediate data. In one implementation, to perform the sequential test automation, test device requirements, such as test scripts, test data, and configuration data are received from a plurality of user devices. In an example, the user may provide the test device requirements through the plurality of user devices. The configuration data is generally used to configure testing environment and comprises database connection profile, such as database (DB) name, DB host, DB username, and DB password for connecting to a database to obtain the test data. The configuration data may further comprise priority of devices and test scripts, and a waiting time for a particular device. The waiting time may indicate approximate time after which a device is available for execution.

Once the test device requirements are obtained, automation scripts may be generated for testing devices. The testing devices are the devices allocated from amongst the plurality of user devices for sequential testing. In an example, the testing devices are allocated based on availability of the user devices and the configuration data. Thereafter, the automation scripts generated for the testing devices are assembled and assigned a namespace. In an example, for the same test device requirements different version of automation scripts with the help of a version manager. This may help in performing the test automation for the plurality of user devices having different platforms installed on them.

These automation scripts, under a same namespace, are then assigned a job identifier (ID) and sent to run queue. In run queue, the automation scripts are stored on registers and executed based on the configuration data. The collection of automation scripts under a same job ID for execution is also referred to as a job. Subsequently, jobs sent to the run queue are assigned an inactive mode and allocation of testing devices is performed. Then, devices from amongst the plurality of user devices that are available for job execution are selected. Hereinafter, the devices, selected from amongst the plurality of user devices, are referred to as testing devices. In an example, the devices which meet the test device requirements received from the user and are available for execution are selected for the job execution.

Once the testing devices are allocated for the job execution, the automation scripts are sent to the testing devices. In case one of the testing devices allotted for execution is not available or execution is dependent on intermediate data, the automation scripts may be kept on hold for a certain time. In case the test devices are available for the execution, the execution process is started by switching a job mode from inactive to active. Upon identifying that the job mode is active, parameters such as, device id, start time, end time, current mode, and data required are initialized.

Further, since test automation is to be performed simultaneously across multiple devices, the automation scripts are scheduled for execution. In an example, the automations scripts are executed as per a sequential schedule. The sequential schedule may be determined based on parameters, such as a waiting time for the testing devices, a priority assigned to the testing devices and the automation scripts, intermediate data, an execution status, and a device status. Once the sequential schedule for the execution is determined, an execution mode is assigned to each of the testing device. The execution mode may be one of a run mode, a wait mode, a complete mode, and a failed mode.

Thereafter, the testing devices in the run mode are instructed to execute the automation scripts based on the sequential schedule. Further, the execution mode of the testing devices, which need intermediate data for execution, is changed to the wait mode. Once the intermediate data for the execution is available, the wait mode is again changed to the run mode and execution of the automation scripts is completed. In this manner, coordination between the testing devices and test automation is performed across multiple devices simultaneously.

Further, in case there is a failed execution due to a fault in the testing device or an error in the automation scripts, a failure recovery is performed. During the failure recovery, execution activities under the same job ID are reconstructed in a newly allocated device. Once the execution reaches to an instance where it had failed, the execution is synchronized with the executions running in other testing devices. Upon synchronization, the executions are carried out by the testing devices till the job is completed.

Thus, the present subject matter performs a sequential testing across the multiple devices simultaneously with automatic exchange of data. Further, requirement of manual exchange of the intermediate data is eliminated by the present subject matter. Also, the present subject matter provides a failure recovery in case of any failed execution. Further, the present subject matter allows the automation testing of the devices even if the devices have different platforms installed on them.

The working of the systems and methods for sequential testing across multiple devices is described in greater detail in conjunction with FIGS. 1-4. It should be noted that the description and drawings merely illustrate the principles of the present subject matter. It will thus be appreciated that those skilled in the art will be able to devise various arrangements that, although not explicitly described or shown herein, embody the principles of the present subject matter and are included within its spirit and scope. Furthermore, all examples recited herein are principally intended expressly to be only for pedagogical purposes to aid the reader in understanding the principles of the present subject matter and are to be construed as being without limitation to such specifically recited examples and conditions. Moreover, all statements herein reciting principles, aspects, and embodiments of the present subject matter, as well as specific examples thereof, are intended to encompass equivalents thereof. While aspects of the systems and methods can be implemented in any number of different computing systems environments, and/or configurations, the embodiments are described in the context of the following exemplary system architecture(s).

FIG. 1 illustrates a network environment 100 implementing an automation testing system 102 for sequential testing across a plurality of devices, according to an embodiment of the present subject matter. Hereinafter, the automated testing system 102 may also be referred to as a system 102.

The system 102 may be implemented in a variety of computing systems, such as a laptop computer, a desktop computer, a notebook, a workstation, a mainframe computer, a server, a network server, and the like. It will be understood that the system 102 may be accessed by users through a plurality of user devices 104-1, 104-2, 104-3, 104-N, collectively referred to as user devices 104 and individually referred to as user device 104. Examples of the user devices 104 include, but are not limited to, a desktop computer, a portable computer, a mobile phone, a handheld device, a workstation. The user devices 104 may be used by various stakeholders or end users of the organization, such as project managers, database administrator, developers and test engineers. As shown in the figure, such user devices 104 are communicatively coupled to the system 102 through a network 106 for facilitating one or more end users to access and/or operate the system 102.

The network 106 may be a wireless network, wired network or a combination thereof. The network 106 can be implemented as one of the different types of networks, such as intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the network 106 may include a variety of network devices, including routers, bridges, servers, computing devices, storage devices, etc.

In one implementation, the system 102 includes a processor 108, a memory 110 coupled to the processor 108, and interfaces 112. The processor 108 may be implemented as one or more microprocessors, microcomputers, microcontrollers, digital signal processors, central processing units, state machines, logic circuitries, and/or any devices that manipulate signals based on operational instructions. Among other capabilities, the processor 108 is configured to fetch and execute computer-readable instructions stored in the memory 110. The memory 110 can include any non-transitory computer-readable medium known in the art including, for example, volatile memory (e.g., RAM), and/or non-volatile memory (e.g., EPROM, flash memory, etc.).

The interface(s) 112 may include a variety of software and hardware interfaces, for example, a web interface, a graphical user interface, etc., allowing the system 102 to interact with the user devices 104. Further, the interface(s) 112 may enable the system 102 respectively to communicate with other computing devices. The interface(s) 112 can facilitate multiple communications within a wide variety of networks and protocol types, including wired networks, for example LAN, cable, etc., and wireless networks such as WLAN, cellular, or satellite. The interface(s) 112 may include one or more ports for connecting a number of devices to each other or to another server.

In one example, the system 102 includes modules 114 and data 116. In one embodiment, the modules 114 and the data 116 may be stored within the memory 110. In one example, the modules 114, amongst other things, include routines, programs, objects, components, and data structures, which perform particular tasks or implement particular abstract data types. The modules 114 and may also be implemented as, signal processor(s), state machine(s), logic circuitries, and/or any other device or component that manipulate signals based on operational instructions. Further, the modules 114 can be implemented by one or more hardware components, by computer-readable instructions executed by a processing unit, or by a combination thereof.

In one implementation, the modules 114 further include an input module 118, a device module 120, a master module 122, an output module 124, and other modules 126. The other modules 126 may perform various miscellaneous functionalities of the system 102. It will be appreciated that such aforementioned modules may be represented as a single module or a combination of different modules.

In one example, the data 116 serves, amongst other things, as a repository for storing data fetched, processed, received and generated by one or more of the modules 114. In one implementation, the data 116 may include, for example, requirement data 128, execution data 130, and other data 132. In one embodiment, the data 116 may be stored in the memory 110 in the form of various data structures. Additionally, the aforementioned data can be organized using data models, such as relational or hierarchical data models. The other data 132 may be used to store data, including temporary data and temporary files, generated by the modules 114 for performing the various functions of the system 102.

In operation, the input module 118 receives test device requirements from the plurality of user devices 104. The test device requirements may include test data, test scripts, and configuration data. The input module 118 uses the configuration data to configure a testing environment. In an example, the configuration module 136 may comprise database connection profiles, waiting time of testing devices, and priority assigned to the testing devices and scripts. In one implementation, the input module 118 may store the test device requirements in requirement data 128 for further usage.

Upon receiving the test device requirements, the input module 118 analyzes the test device requirements to generate automation scripts for test automation. In one implementation, the input module 118 may obtain the test scripts present in the test device requirements to construct the automation scripts. The input module 118 also considers software version so that version specific automation scripts are generated and test automation can be performed on different version of software installed on the plurality of user devices 104. Also, with the help of the version manager, the input module 118 may generate the automation scripts that can be used for the test automation of the plurality of user devices 104 having different platforms installed on them. Further, the input module 118 assembles the automation scripts of a particular test case under a same namespace and assigns a job ID. The automation scripts for execution under the same job id are referred to as a job. Further, various components and functioning of the input module 118 are discussed in conjunction with FIG. 1(b).

Once the automation scripts are ready for execution, the device module 120 allocates testing devices, from amongst the plurality of user devices 104 based on availability of the plurality of user devices 104 and the test device requirements. In an example, the plurality of user devices 104 may have same platform installed on them. In another example, the plurality of user devices 104 may have different platforms on them. In one implementation, the device module 120 monitors connection with the plurality of user devices 104 and identifies the devices that are available for the test automation. The device module 120 keeps the master module 122 updated about the availability of the devices. In an example, the device module 120 allocates the available devices for testing which satisfies requirements for testing specified in the test device requirements. Further, various components and functioning of the device module 120 are discussed in conjunction with FIG. 1(c).

Subsequently, the master module 122 determines a sequential schedule based on sequence parameters, such as a waiting time for the testing devices, a priority assigned to the testing devices and the automation scripts, intermediate data, an execution status, and a device status. The intermediate data may be understood as data resulted from execution of the automation scripts which may be used by one or more testing devices in order to complete execution of the test automation scripts on them. The execution status may indicate running and/or completion status of executions and comprise predefined rules for execution. In an example, the predefined rules may specify that execution of the automation scripts by a second testing device, D2, should start once a first testing device, D1, has finished its execution. In another example, the predefined rules may specify that execution should start on D2 after 15 minutes execution of the automation scripts on D1. Further, the device status indicates availability user devices 104 for execution.

In an example, the sequence parameters may be obtained from the configuration data provided by the user and execution data maintained by an execution tracker. Once the sequential schedule is determined, the master module 122 assigns an execution mode to each of the testing devices based on the sequential schedule. The execution mode may be one of a run mode, a wait mode, a complete mode, and a failed mode. Thereafter, the jobs are executed as per the sequential schedule and the execution mode assigned to the testing device. During execution, the master module 122 maintains a track of executions and changes in the execution mode assigned to the testing devices. In case the master module 122 identifies that the execution mode is changes from the run mode to the wait mode and the intermediate data is needed for the execution, the master module 122 provides the intermediate data to the testing device put on the wait mode. Further, if the intermediate data is not available with the master module 122, the master module 122 may wait for the intermediate data created from other executions. Upon obtaining the intermediate, the master module 122 may then send the data to the intended testing device for execution. Thus, a coordinated and optimized sequential testing is performed across multiple user devices 104.

In one implementation, the master module 122 performs a failure recovery whenever a failed execution is identified. The execution may fail due to some problem in the script or a faulty device. In such case, the master module 122 may assign another testing device, for the sequential testing, which is available for the execution. Thereafter, the master module 122 may generate a reconstruction phase for the failed execution. In the reconstruction phase, other testing devices are assigned the wait mode and the failed execution is reconstructed. Once the reconstruction of failed execution reached a point where it failed, the executions put on wait are synchronized and then the testing devices are instructed to execute the job assigned to them. Further, various components and functioning of the master module 122 are discussed in conjunction with FIG. 1(d).

The system 102 further comprises an output module 124. The output module 124 acts as an interface of the system 102 and provides responses received from the modules to the user.

Figure 1B:
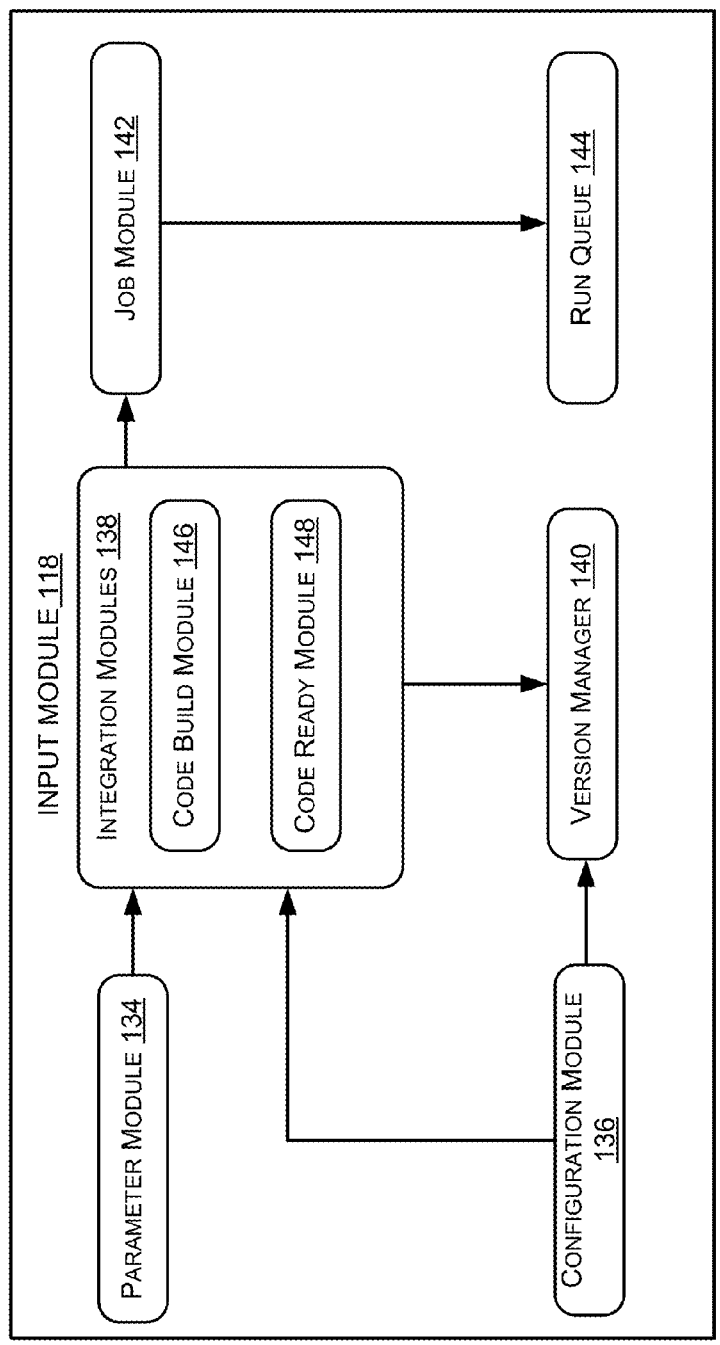
FIG. 1(b) illustrates various components of an input module, according to an embodiment of the present subject matter.

FIG. 1(b) illustrates various components of an input module 118, according to an embodiment of the present subject matter. As shown in FIG. 1(b), the input module 118 comprises a parameter module 134, a configuration module 136, an integration module 138, a version manager 140, a job module 142, and a run queue 144. In one implementation, the parameter module 134 receives test scripts and test data from the user through the devices. The parameter module 134 may receive the test scripts and the test from different sources, such as excel sheets, databases, and third party tools.

Further, the configuration module 136 obtains configuration data from the user devices 104. The configuration data helps in configuring a testing environment. The configuration data may include database connection profiles, priority of devices and test scripts, and waiting time for devices. For example, the configuration data may include database (DB) name, DB Host, DB username and DB Password for connecting to a database and obtaining test data from the databases. The priority of the test devices and test scripts allows the master module 122 to determine sequence in which the test execution is to be performed. Also, the waiting time for the test devices is used by the master module 122 to ascertain the devices that are available for execution of test scripts. In an example, the master module 122 analyzes the configuration data and keeps the automation scripts on hold for a time predefined time determined based on the waiting time. In one implementation, the configuration data may be then stored in the requirement data 128 so that the configuration data is accessible to all the modules present in the system 102. Further, any change in the configuration data is reflected across all the modules. It may be noted that setups in the configuration module 136 can also be overwritten programmatically, allowing the user to take complete control over the automation test execution process.

Thereafter, integration module 138 receives the test scripts based on version provided in the configuration data. As shown in FIG. 1(b), the integration module 138 comprises a code build module 146 and a code ready module 148. The code build module 146 constructs the automation script that is executable in the testing devices. The code build module 146 is scalable for each of the specific computing device, and operates independently to generate the automation script. Also, the code build module 146 may allow the flexibility of adding any new sub module specific to a new device without affecting the existing design with minimal changes. Further, a version manager 140 may also be used along with the code build module 146 to generate version specific test execution script, which allows the user to test on different versions of the software and on different platforms installed in the plurality of devices.

Upon generation of the automation script, the code ready module 148 may assemble all the automation scripts of a given test case under a namespace to ensure that the scripts generated by the code build module 146 are execution ready. Once the automation scripts are assembled and assigned a namespace, the automation scripts are sent to the job module 142.

The job module 142 replaces the namespace with a Job ID. The Job ID is unique for each test case and all testing activities are controlled and tracked based on the Job ID. The Job ID generally remains the same till all the executions have been finished.

Further, the test cases with the Job ID are stored by the run queue 144 in its registers. Based on the configuration data, the job execution is done as per the instruction provided by the user i.e. to start running immediately or to be kept on hold for a certain time.

Figure 1C:
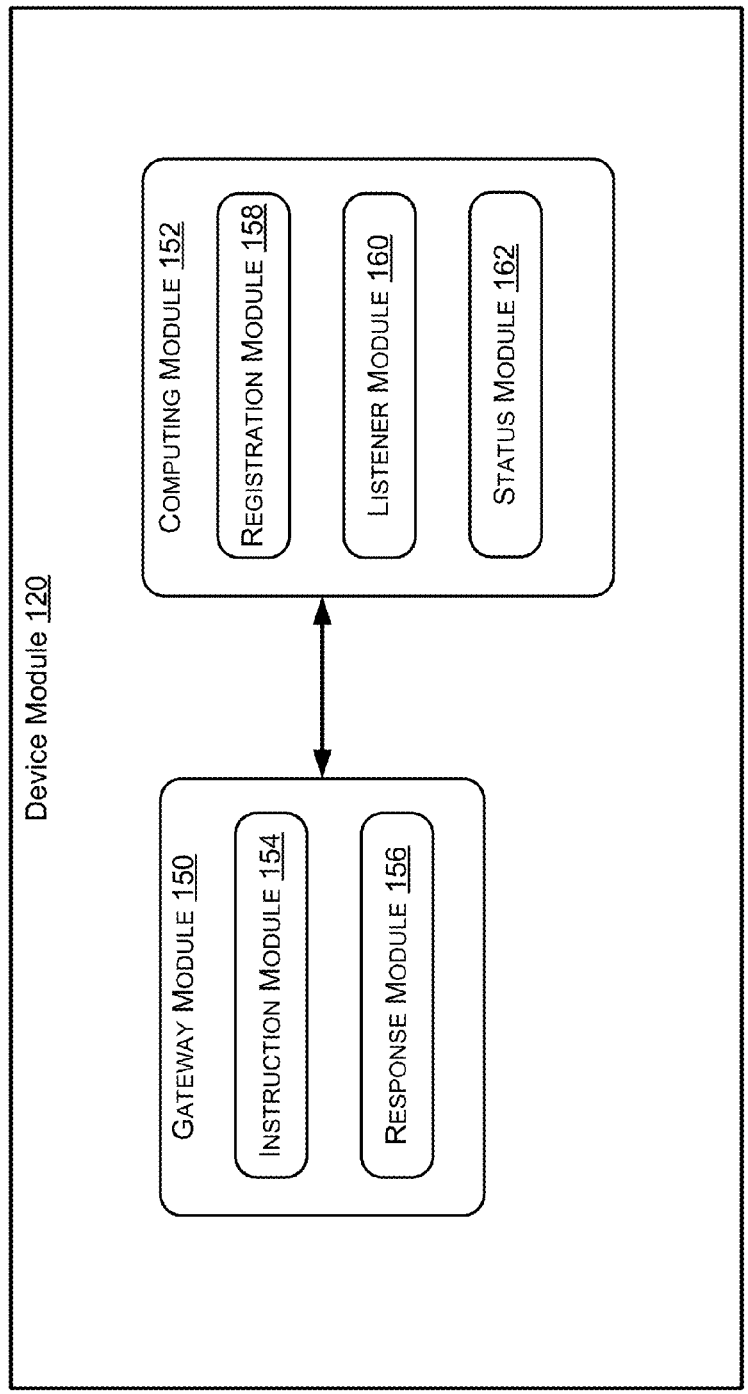
FIG. 1(c) illustrates various components of a device module, according to an embodiment of the present subject matter.

FIG. 1(c) illustrates various components of a device module 120, according to an embodiment of the present subject matter. As shown in FIG. 1(c), the device module 120 comprises a gateway module 150 and a computing module 152.

The gateway module 150 converts the instruction received from the master module 122 so that a destination device can understand the instructions.

The instructions module 154 maintains device specific instructions that are understandable by the destination computing device.

The response module 156 receives response from the user devices 104. The response may comprise metadata, such as a device id from which the response is coming, and a unique id of intermediate data.

The computing module 152 comprises details about the different computing devices available for testing using this system 102. The computing module 152 further comprises three sub modules a registration module 158, a listener module 160, and a status module 162. The registration module 158 comprises details of all the devices which can be used for automation activities by this system 102. The listener module 160 monitors the connection with all the computing devices. A signal is received from the computing device to ensure that the connection between the device module 120 and the computing device is normal and operational. Any issue detected in the connection, by the listener module 160, is reported to the Status module 162. The listener module 160 may keep monitoring the signal continuously in background The status module 162 gets updates from the listener module 160 and keeps the latest record of the device status. The status module 162 provides details about execution to the master module 122. The details may include number of devices running, available or have been kept in waiting.

Figure 1D:
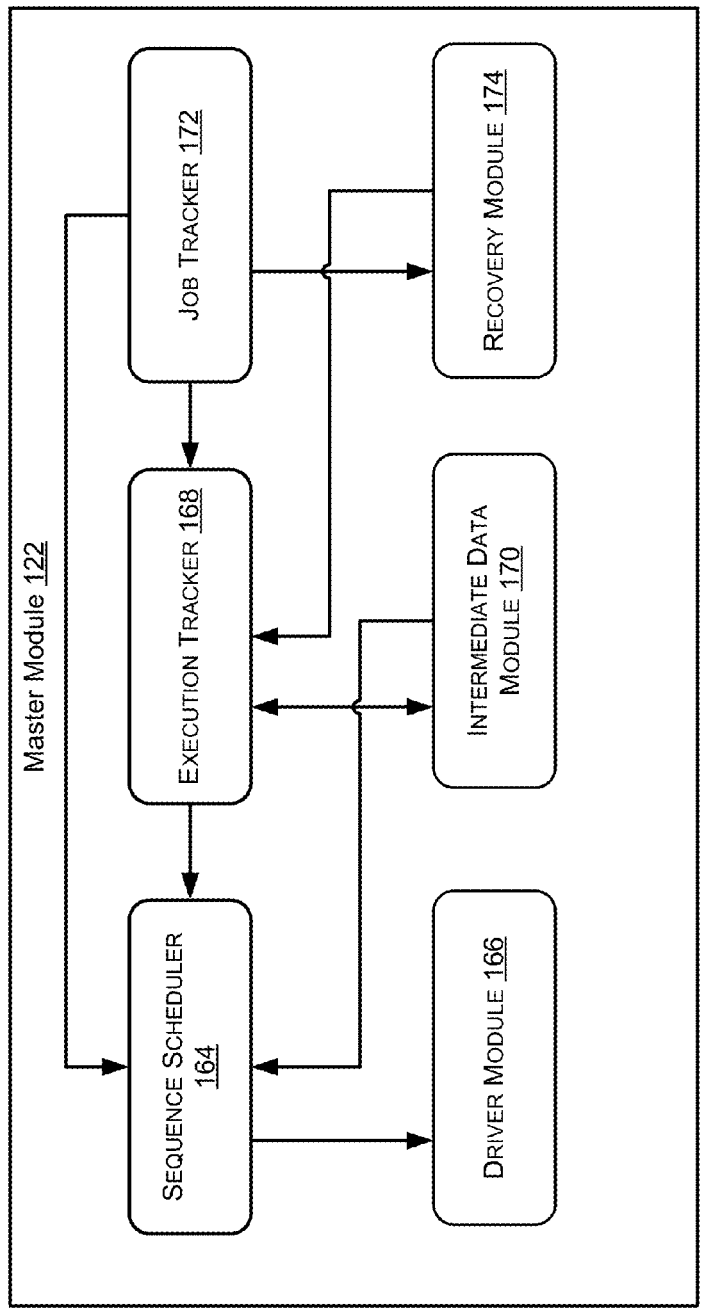
FIG. 1(d) illustrates various components of a master module, according to an embodiment of the present subject matter.

FIG. 1(d) illustrates various components of a master module 122, according to an embodiment of the present subject matter. As shown in FIG. 1(d), the master module 122 comprises a sequence scheduler 164, a driver module 166, an execution tracker 168, an intermediate data module 170, a job tracker 172, and a recovery module 174.

All test scripts under a job will be executed in different testing devices, the sequence of execution and co-ordination between these devices are maintained by the sequential scheduler. In one implementation, the sequence scheduler 164 determines the sequence of execution based on at least one sequence parameter. The sequence parameters may include time, priority, intermediate data execution status, and device Status. The sequence parameters are obtained from the configuration module 136, the execution tracker 168, the intermediate data module 170, and the device module 120. Once the sequence of the execution is ready, the sequence scheduler 164 assigns an execution mode to each of the testing devices. The execution mode may be one of run, wait, complete, and failed.

Subsequently, the driver module 166 sends the execution mode to the target testing device. In case where the intermediate data is needed for execution and is available for the execution, the driver module 166 sends the intermediate test data along with the execution mode to the target testing device through the device module 120. The intermediate data module 170 obtains intermediate data from device response and stores in the execution data 130 till the data belonging to the job is completed. The intermediate data can be transferred to other computing device doing the same job. The intermediate data module 170 facilitates exchange of data between different computing platforms.

To keep track of all the executions that are taking place in the target testing devices, the execution tracker 168 stores details, such as registrations Id, job Id, script name, device Id, execution start time, execution end time, and waiting time. The execution tracker 168 also stores time and execution status of a script, which are used for calculating sequence of execution of a job.

The job tracker 172 maintains track of job execution status. The job tracker 172 module does the tracking of jobs that are running, stopped, and failed or in a reconstruction phase.

Further, it may be possible that an execution process may fail. In such cases, the failure recovery facilitates to recover from failure. The failure may be due to the device or due to the execution script. The recovery module 174 reconstructs all the execution activities in a newly allocated device under the same job ID. Once the failed execution reaches to the instance where it had failed, it synchronizes with the other devices of the job and continues executing till the job is completed.

Thus, the system 102 performs the sequential testing across multiple devices along with automatic exchange of the intermediate data between the testing devices. Further, the system 102 coordinates between the executions running in different testing devices. The system 102 also provides the failure recovery in case a failed execution is detected.

Figure 2:
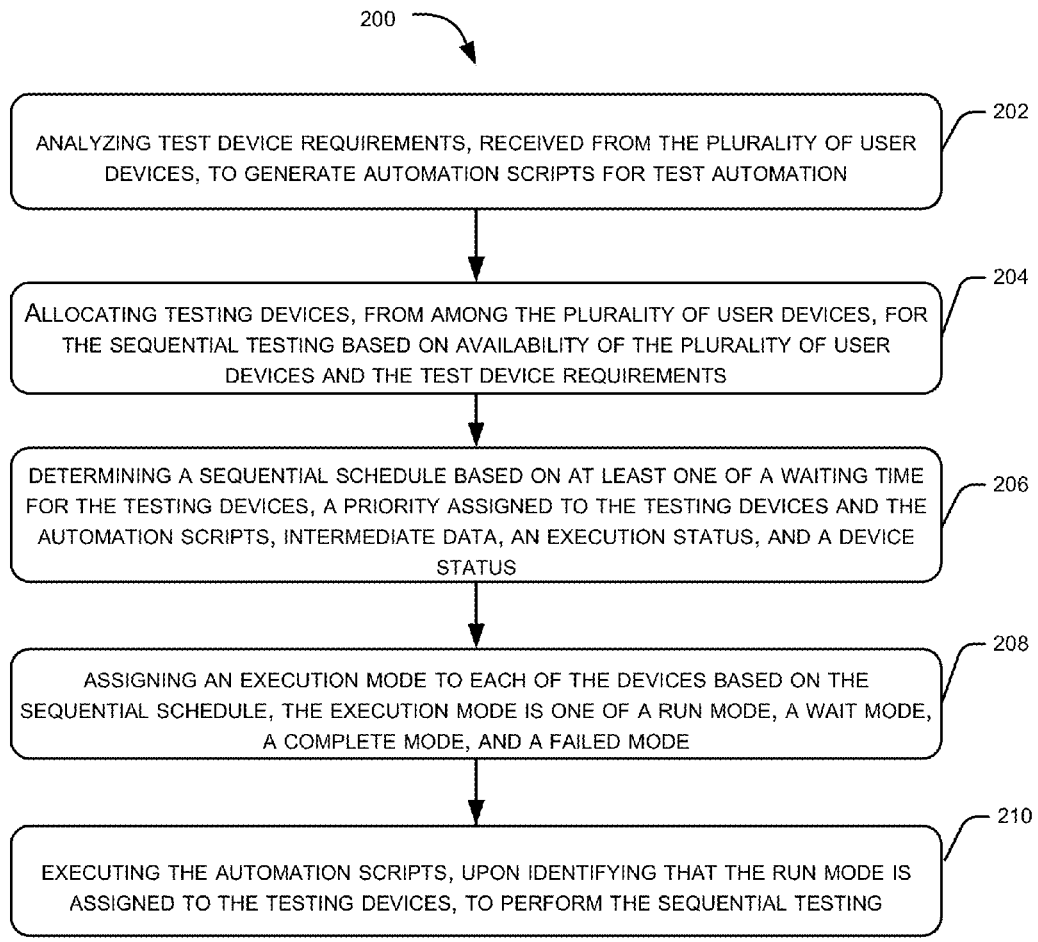
FIG. 2 illustrates exemplary computer implemented methods for sequential testing across multiple devices, according to an embodiment of the present subject matter.

FIG. 2 illustrates exemplary computer implemented methods for sequential testing across a plurality of devices, according to an embodiment of the present subject matter.

Figure 3:
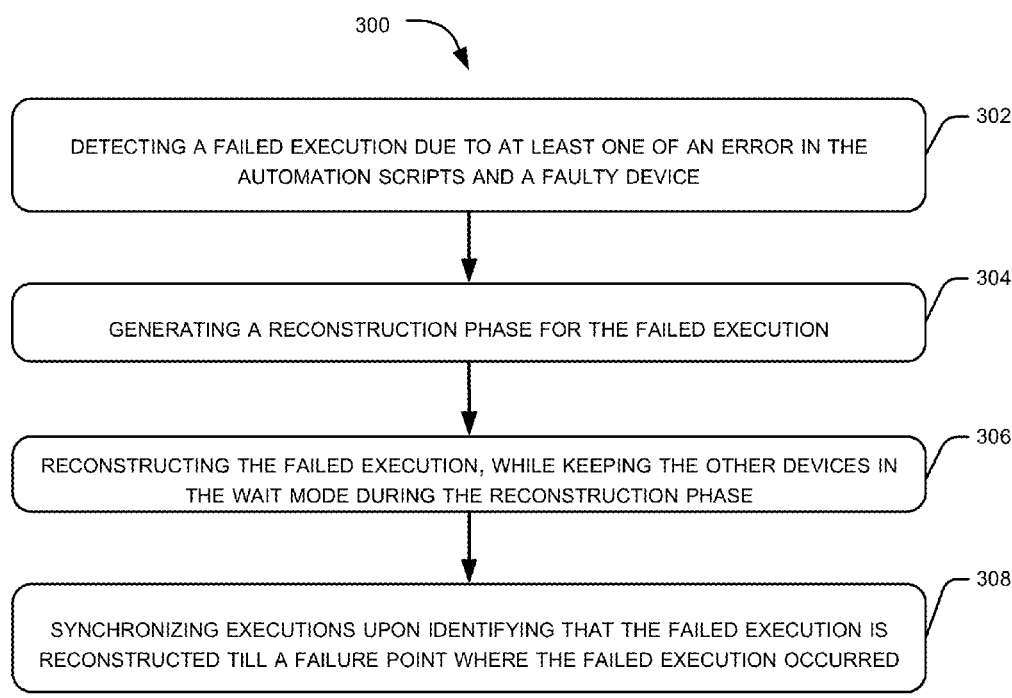
FIG. 3 illustrates exemplary computer implemented methods for performing failure recovery, according to an embodiment of the present subject matter.

FIG. 3 illustrates exemplary computer implemented methods for performing failure recovery, according to an embodiment of the present subject matter.

The methods 200 and 300 may be described in the general context of computer executable instructions. Generally, computer executable instructions can include routines, programs, objects, components, data structures, procedures, modules, and functions, which perform particular functions or implement particular abstract data types. The methods 200 and 300 may also be practiced in a distributed computing environment where functions are performed by remote processing devices that are linked through a communication network. In a distributed computing environment, computer executable instructions may be located in both local and remote computer storage media, including memory storage devices.

The order in which the methods 200 and 300 are described is not intended to be construed as a limitation, and any number of the described method blocks can be combined in any order to implement the methods 200 and 300 or alternative methods. Additionally, individual blocks may be deleted from the methods 200 and 300 without departing from the spirit and scope of the subject matter described herein. Furthermore, the methods 200 and 300 can be implemented in any suitable hardware, software, firmware, or combination thereof.

With reference to method 200 as depicted in FIG. 2, as shown in block 202, test device requirements received from the plurality of user devices 104 are analyzed to generate an automation script for each of the testing device. In one example, the plurality of user devices 104 may have different platforms installed on them. In another example, the plurality of user devices 104 may have same platforms installed on them. The test device requirements may comprise test scripts, test data and configuration data provided by the user. Once the test device requirements are received, the automation scripts are generated. In one implementation, the integration module 138 may generate the automation scripts for the plurality of user devices 104 having same or different platforms using the same test parameters with the help of the version manager 140. Further, the automation scripts are assembled under a namespace and assigned a job ID. The job ID is a unique identifier throughout the test execution process, which allows the system 102 to track and control the automation process. Subsequently, the job, i.e., the automation scripts under a job ID is sent to the run queue 144.

At block 204, testing devices, from amongst the plurality of user devices 104, are allocated for automated sequential testing based on the test device requirements and availability of the plurality of user devices 104. In one implementation, the master module 122 makes a request to the device module 120 with all the device requirements and waits for the response. In case, the device module 120 has availability of the testing devices, the device module 120 allocates the testing devices for the job and returns a device ID to the Job tracker 172. If the devices are not available, the master module 122 receives a notification indicating unavailability of the testing devices. Once the testing devices are allocated by the device module 120, the master module 122 dispatches the automation scripts to the testing devices through the devices module.

At block 206, a sequential schedule is determined based on at least one of a waiting time for the testing devices, a priority assigned to the testing devices and the automation scripts, intermediate data, an execution status, and a device status. In one implementation, the sequential scheduler of the master module 122 receives the device IDs of a job from execution tracker 168 and uses parameters such as a priority of a script, a time, intermediate data, a device status, and execution status to schedule the mode and order of the testing devices. Further, the sequence scheduler 164 keeps track of the testing devices, for example, which all are kept in wait and the reason for their waiting. In an example, the testing device may wait for the intermediate data to proceed further. If the intermediate data is available, the master module 122 retrieves the intermediate data from the Intermediate module and dispatches to the testing devices.

At block 208, an execution mode is assigned to each of the device based on the sequential schedule. The execution mode is one of a wait mode, a run mode, a complete mode, and a failed mode. In an example, the testing devices available for the test automation are assigned the run mode. In another example, the testing devices waiting for the intermediate data are assigned the wait mode. Once the intermediate data is available with the testing device for execution, the execution mode of the testing device is changes from the wait mode to the run mode. In this manner, co-ordination between different testing devices is achieved.

At block 210, the automation script is executed, upon identifying that the run mode is assigned to the testing devices, to perform the automated sequential testing. In one implementation, the testing devices in the run mode executes the automation scripts if the intermediate data needed for the execution is available With reference to method 300 as depicted in FIG. 3, as shown in block 302, a failed execution is detected. The failed execution may occur due to a faulty device or an error in the automation script. In one implementation, if a job fails due to the failure of device or due an error in the automation script, the job tracker 172 decides based on the configuration data whether or not to reconstruct a failed execution. In case, the failed execution is to be reconstructed, the job tracker 172 makes a request to the device module 120 to allocate another testing device. On successful allocation, the automation scripts are sent to the execution tracker 168 for registration and initialization.

At block 304, a reconstruction phase is generated for the failed execution. In one implementation, the recovery module 174 generates the reconstruction phase in which the failed execution is reconstructed. In an example, when the testing device fails and in a phase of reconstruction, the testing device takes less time using logs than the execution of original script, because there is no waiting time for the intermediate data as the data are already present with the intermediate module.

At block 306, the failed execution is reconstructed while keeping the other devices in wait mode during reconstruction phase. In one implementation, in the reconstruction phase, all the other testing devices of the job are kept in the wait mode till the recovery reaches to the instance where it had failed.

At block 308, executions are synchronized upon identifying that the reconstructed script is executed till a failure point. In one implementation, once the reconstruction is done, the recovery module 174 synchronizes the new testing device with the other devices. Further, the testing devices are instructed to continue executing the jobs assigned to them. In this manner, a failure recover mechanism is implemented in the present subject matter.

Computer System

Figure 4:
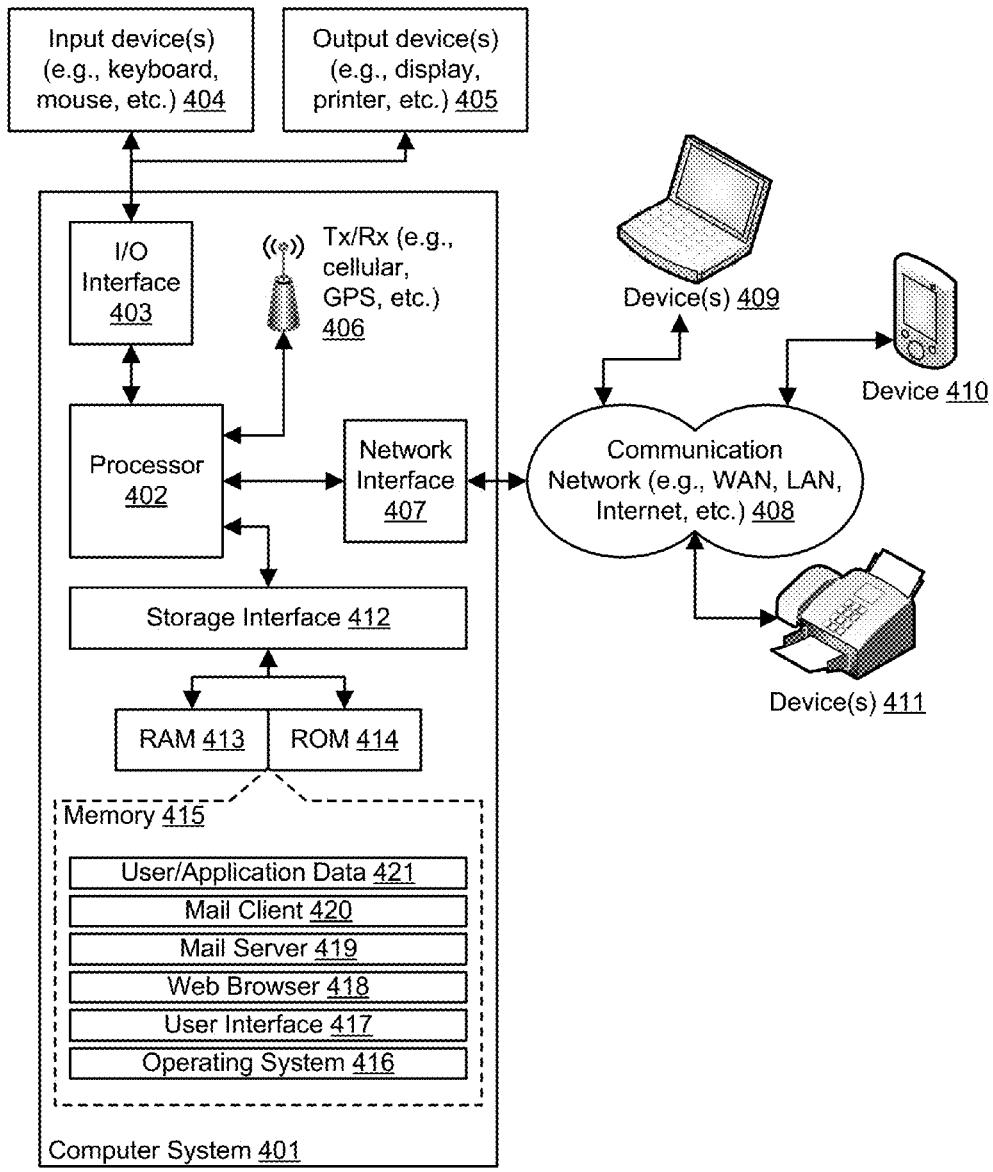
FIG. 4 is a block diagram of an exemplary computer system for implementing embodiments consistent with the present disclosure.

FIG. 4 is a block diagram of an exemplary computer system for implementing embodiments consistent with the present disclosure. Variations of computer system 401 may be used for implementing any of the devices presented in this disclosure. Computer system 401 may comprise a central processing unit ("CPU" or "processor") 402. Processor 402 may comprise at least one data processor for executing program components for executing user- or system-generated requests. A user may include a person, a person using a device such as such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 402 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 402 may be disposed in communication with one or more input/output (I/O) devices via I/O interface 403. The I/O interface 403 may employ communication protocols/methods such as, without limitation, audio, analog, digital, monaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 403, the computer system 401 may communicate with one or more I/O devices. For example, the input device 404 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 405 may be a printer, fax machine, video display (e.g., cathode ray tube (CRT), liquid crystal display (LCD), light-emitting diode (LED), plasma, or the like), audio speaker, etc. In some embodiments, a transceiver 406 may be disposed in connection with the processor 402. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 318-PMB9800, or the like), providing IEEE 802.11a/b/g/n, Bluetooth, FM, global positioning system (GPS), 2G/3G HSDPA/HSUPA communications, etc.

In some embodiments, the processor 402 may be disposed in communication with a communication network 408 via a network interface 407. The network interface 407 may communicate with the communication network 408. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 408 may include, without limitation, a direct interconnection, local area network (LAN), wide area network (WAN), wireless network (e.g., using Wireless Application Protocol), the Internet, etc. Using the network interface 407 and the communication network 408, the computer system 401 may communicate with devices 410, 411, and 412. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 401 may itself embody one or more of these devices.

In some embodiments, the processor 402 may be disposed in communication with one or more memory devices (e.g., RAM 413, ROM 414, etc.) via a storage interface 412. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

The memory devices may store a collection of program or database components, including, without limitation, an operating system 416, user interface application 417, web browser 418, mail server 419, mail client 420, user/application data 421 (e.g., any data variables or data records discussed in this disclosure), etc. The operating system 416 may facilitate resource management and operation of the computer system 401. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 417 may facilitate display, execution, interaction, manipulation, or operation of program components through textual or graphical facilities. For example, user interfaces may provide computer interaction interface elements on a display system operatively connected to the computer system 401, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 401 may implement a web browser 418 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol); secure sockets layer (SSL), Transport Layer Security (TLS), etc. Web browsers may utilize facilities such as AJAX, DHTML, Adobe Flash, JavaScript, Java; application programming interfaces (APIs), etc. In some embodiments, the computer system 401 may implement a mail server 419 stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 401 may implement a mail client 420 stored program component. The mail client may be a mail viewing application, such as Apple Mail, Microsoft Entourage, Microsoft Outlook, Mozilla Thunderbird, etc.

In some embodiments, computer system 401 may store user/application data 421, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

The specification has described a method and a system for sequential testing across a plurality of devices. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A computer implemented method for sequential testing across multiple devices, the method comprising:
    analyzing test device requirements, received from a plurality of user devices, to generate automation scripts for test automation;
    allocating testing devices, from among the plurality of user devices, for the sequential testing based on availability of the plurality of user devices and the test device requirements;
    determining a sequential schedule based on at least one of a waiting time for the testing devices, a priority assigned to the testing devices or the automation scripts, intermediate data, an execution status, and a device status;
    executing the automation scripts based on the sequential schedule, upon identifying that an execution mode corresponding to a run mode is assigned to the testing devices, to perform the sequential testing; and
    obtaining, from at least one user device of the plurality of user devices, intermediate data for at least one of the testing devices, upon ascertaining a change in the execution mode of the at least one of the testing devices from the run mode to a wait mode, wherein the execution of the automation scripts for the at least one of the testing devices is dependent on the intermediate data, and wherein platform of the at least one user device being different from the platform of the at least one of the testing devices.

2. The computer implemented method according to claim 1 further comprises:
    assigning the execution mode to each of the testing devices based on the sequential schedule, wherein the execution mode is the run mode, the wait mode, a complete mode, or a failed mode.

3. The computer implemented method according to claim 1, wherein at least one of the plurality of user devices has a different platform.

4. The computer implemented method according to claim 1, wherein the executing the automation scripts comprises:
    maintaining a track of executions and the execution mode assigned to each of the testing device; and
    resuming execution of the automation scripts upon receiving the intermediate data.

5. The computer implemented method according to claim 1 further comprises assigning another testing device, from the plurality of user devices, for the sequential testing upon identifying a failed execution.

6. The computer implemented method according to claim 5, wherein the assigning further comprises:
    detecting a failed execution due to at least one of an error in the automation scripts or a faulty device;
    generating a reconstruction phase for the failed execution;
    reconstructing the failed execution, while keeping the other devices in the wait mode during the reconstruction phase; and
    synchronizing executions upon identifying that the failed execution is reconstructed until a failure point where the failed execution occurred.

7. An automated testing system for sequential testing across multiple devices comprising:

one or more hardware processors; and a computer-readable medium storing instructions that, when executed by the one or more hardware processors, cause the one or more hardware processors to perform operations comprising:

analyzing test device requirements, received from a plurality of user devices, to generate automation scripts for test automation;

allocating testing devices, from among the plurality of user devices, for the sequential testing based on availability of the plurality of user devices and the test device requirements;

determining a sequential schedule based on at least one of a waiting time for the testing devices, a priority assigned to the testing devices or the automation scripts, intermediate data, an execution status, and a device status;

executing the automation scripts based on the sequential schedule, upon identifying that an execution mode corresponding to a run mode is assigned to the testing devices, to perform the sequential testing; and obtaining, from at least one user device of the plurality of user devices, intermediate data for at least one of the testing devices, upon ascertaining a change in the execution mode of the at least one of the testing devices from the run mode to a wait mode, wherein the execution of the automation scripts for the at least one of the testing devices is dependent on the intermediate data, and wherein platform of the at least one user device being different from the platform of the at least one of the testing devices.

8. The system according to claim 7, wherein the operations further comprise:

assigning the execution mode to each of the testing devices based on the sequential schedule, wherein the execution mode is the run mode, the wait mode, a complete mode, or a failed mode.

9. The system according to claim 7, wherein at least one of the plurality of user devices has a different platform.

10. The system according to claim 7, wherein the operations of the executing the automation scripts further comprise:

maintaining a track of executions and the execution mode assigned to each of the testing device; and resuming execution of the automation scripts upon receiving the intermediate data.

11. The system according to claim 7, wherein the operations further comprises assigning another testing device, from the plurality of user devices, for the sequential testing upon identifying a failed execution.

12. The system according to claim 11, wherein the operations of the assigning further comprise:

detecting a failed execution due to at least one of an error in the automation scripts or a faulty device;

generating a reconstruction phase for the failed execution;

reconstructing the failed execution, while keeping the other devices in the wait mode during the reconstruction phase; and synchronizing executions upon identifying that the failed execution is reconstructed until a failure point where the failed execution occurred.

13. A non-transitory computer-readable medium storing instructions for sequential testing across multiple devices, wherein upon execution of the instructions by one or more hardware processors, the hardware processors perform operations comprising:

analyzing test device requirements, received from a plurality of user devices, to generate automation scripts for test automation;

allocating testing devices, from among the plurality of user devices, for the sequential testing based on availability of the plurality of user devices and the test device requirements;

determining a sequential schedule based on at least one of a waiting time for the testing devices, a priority assigned to the testing devices or the automation scripts, intermediate data, an execution status, and a device status;

executing the automation scripts based on the sequential schedule, upon identifying that an execution mode corresponding to a run mode is assigned to the testing devices, to perform the sequential testing; and obtaining, from at least one user device of the plurality of user devices, intermediate data for at least one of the testing devices, upon ascertaining a change in the execution mode of the at least one of the testing devices from the run mode to a wait mode, wherein the execution of the automation scripts for the at least one of the testing devices is dependent on the intermediate data, and wherein platform of the at least one user device being different from the platform of the at least one of the testing devices.

14. The non-transitory computer-readable medium according to claim 13, wherein the operations further comprise:

assigning the execution mode to each of the testing devices based on the sequential schedule, wherein the execution mode is the run mode, the wait mode, a complete mode, a failed mode.

15. The non-transitory computer-readable medium according to claim 13, wherein at least one of the plurality of user devices has a different platform.

16. The non-transitory computer-readable medium according to claim 13, wherein the operations of the executing the automation scripts further comprise:

maintaining a track of executions and the execution mode assigned to each of the testing device; and resuming execution of the automation scripts upon receiving the intermediate data.

17. The non-transitory computer-readable medium according to claim 13, wherein the operations further comprises assigning another testing device, from amongst the plurality of user devices, for the sequential testing upon identifying a failed execution.

18. The non-transitory computer-readable medium according to claim 13, wherein the operations further comprise:

detecting a failed execution due to at least one of an error in the automation scripts or a faulty device;

generating a reconstruction phase for the failed execution;

reconstructing the failed execution, while keeping the other devices in the wait mode during the reconstruction phase; and synchronizing executions upon identifying that the failed execution is reconstructed until a failure point where the failed execution occurred.

* * * * *